(12) United States Patent
Merrill

(10) Patent No.: US 6,689,926 B2
(45) Date of Patent: Feb. 10, 2004

(54) PROCESS FOR PURIFYING STYRENE MONOMER FEEDSTOCK PRIOR TO POLYMERIZATION

(75) Inventor: James T. Merrill, Katy, TX (US)

(73) Assignee: Fina Technology, Inc., Houston, TX (US)

( * ) Notice: Subject to any disclaimer, the term of this patent is extended or adjusted under 35 U.S.C. 154(b) by 44 days.

(21) Appl. No.: 10/074,387

(22) Filed: Feb. 12, 2002

(65) Prior Publication Data

US 2003/0163009 A1 Aug. 28, 2003

(51) Int. Cl.$^7$ .............. C07C 5/10; C07C 7/148; C07C 7/167
(52) U.S. Cl. .......... 585/259; 585/258; 585/261; 585/262; 585/860; 585/862; 585/863
(58) Field of Search ............ 585/258, 259, 585/261, 262, 860, 862, 863

(56) References Cited

U.S. PATENT DOCUMENTS

| | | | |
|---|---|---|---|
| 4,466,905 A | 8/1984 | Butler et al. ............ 585/3 |
| 4,929,778 A | 5/1990 | Roling ............ 585/3 |
| 5,156,816 A | 10/1992 | Butler et al. ............ 442/141 |
| 5,221,461 A | 6/1993 | Henrici et al. ............ 208/48 |
| 5,221,498 A | 6/1993 | Reid et al. ............ 252/403 |
| 5,221,764 A | 6/1993 | Roling ............ 560/205 |
| 5,282,957 A | 2/1994 | Wright et al. ............ 208/48 |
| 5,396,004 A | 3/1995 | Arhancet et al. ............ 585/5 |
| 5,426,257 A | 6/1995 | Arhancet ............ 585/5 |
| 6,024,894 A | 2/2000 | Arhancet ............ 252/404 |

FOREIGN PATENT DOCUMENTS

| | | |
|---|---|---|
| EP | 0240297 | 10/1987 |
| EP | 0594341 | 4/1994 |
| EP | 0594431 | 4/1994 |
| JP | 49-7229 | * 1/1974 |

OTHER PUBLICATIONS

The English translation of JP 49–7229.*

* cited by examiner

Primary Examiner—Thuan D Dang
(74) Attorney, Agent, or Firm—Bradley A. Misley

(57) ABSTRACT

A process is disclosed which provides for the reduction of phenylacetylene levels in styrene monomer feedstreams, which process utilizes a normal styrene inhibitor additive, such as an hydroxylamine, injected into the styrene monomer feedstream immediately upstream of the phenylacetylene reduction reactor.

9 Claims, 1 Drawing Sheet

PROCESS FOR PURIFYING STYRENE MONOMER FEEDSTOCK PRIOR TO POLYMERIZATION

FIELD OF THE INVENTION

This invention relates to the field of monovinylaromatic compound purification and polymerization, and more particularly discloses a process for the reduction of phenylacetylene contaminants in crude styrene feedstock prior to polymerization of the styrene into polystyrene.

BACKGROUND OF THE INVENTION

Of all the thermoplastics manufactured today, probably the most versatile and most widely utilized class of materials is polymerized monovinyl aromatic compounds such as polystyrene, polymerized alpha-methyl styrene, and polymers of ring-substituted styrenes.

Some of the most common uses of these compounds (often referred to collectively as "styrenes" or "polystyrenes") are for manufacturing food and beverage containers, food wrap, and children's toys. One disadvantage associated with such uses of polystyrene is the residual monomer and other contaminants in the polymer, which may contribute to off-taste, odor, off-color and other adulteration or degradation of the polymer quality.

A particularly offensive contaminant associated with such undesirable properties in polystyrene is unreacted vinyl aromatic monomer, usually styrene monomer. One of the causes of unreacted monomer is directly related to the presence of phenylacetylene in the styrene feedstock going into the polymerization reactor system.

In the manufacture of monovinyl aromatic polymer compounds, and more particularly in the manufacture of polystyrene (PS), benzene is reacted with ethylene to form ethylbenzene (EB). This molecular compound is then dehydrogenated in an EB dehydrogenation, or "dehydro", unit to form a crude styrene product. The crude styrene product is subsequently purified to produce styrene monomer product. The styrene monomer is then polymerized, usually in the presence of a polymerization initiator or catalyst, to form the final polystyrene raw material.

Unfortunately, phenylacetylene, one of the undesirable side products of the EB dehydro unit, is formed when EB is dehydrogenated one step too far. Consequently, the product stream from the dehydro unit contains styrene, EB, and traces of phenylacetylene. The EB is easily removed by conventional processes, such as common distillation, leaving styrene monomer and phenylacetylene. The removal of phenylacetylene cannot be accomplished by simple or conventional means such as distillation and has heretofore been a difficult and very costly process.

The presence of phenylacetylene in styrene monomer has undesirable consequences regardless of whether the method of polymerization utilized is anionic, or free-radical polymerization. During anionic polymerization, phenylacetylene which is slightly acidic, consumes a stoichiometric amount of catalyst, such as butyllithium, wherein one molecule of butyllithium is removed from the polymerization process by each molecule of phenylacetylene. This loss of catalyst can be costly and causes the concentration of catalyst to be difficult to control. This, in turn, causes the molecular weight of the polystyrene to be difficult to control and can result in an increase in the concentration of low molecular weight polymer and even leave unreacted styrene in the polystyrene.

During free-radical polymerization, the presence of phenylacetylene can have detrimental effects on chain length and polymerization rate, because it is a poor chain transfer agent. Consequently, in the manufacture of polystyrene beads, which are used to make expanded polystyrene (EPS) or "foamed" polystyrene, significant amounts of residual styrene are left in the beads. Styrene creates undesirable taste, color, and odor, even when present in only minute amounts in the polymer.

Thus, the presence of phenylacetylene in styrene monomer has adverse effects on cost, control of the polymerization process, and purity of the resulting polystyrene. The presence of phenylacetylene in polystyrene also results in olefinic bonds in the backbone of the polymer which can increase cross-linking and cause more rapid oxidation of the polymer, both of which degrade the polymer significantly.

In the free-radical polymerization of styrene, as the concentration of styrene decreases during the polymerization process, the relative concentration of phenylacetylene naturally rises. Since phenylacetylene acts as a polymerization inhibitor, the polymerization process is undesirably affected.

Catalytic attempts at reducing the phenylacetylene levels in styrene monomer streams have involved the injection of high levels of hydrogen gas into the monomer in an attempt to reduce the phenylacetylene to styrene. Any hydrogen added into the stream in stoichiometric excess of the phenylacetylene present there results in conversion of significant amounts of styrene back into ethylbenzene, causing a lower styrene concentration and a lower conversion rate. Significant reductions in phenylacetylene were achieved only at the expense of styrene conversion to EB and resultant loss of styrene production.

One patent directed to the use of hydrogen gas for phenylacetylene reduction (PAR) is U.S. Pat. No. 5,156,816 granted to Butler et al on Oct. 20, 1992, which teaches a PAR process based upon the use of a catalytic bed with multiple hydrogen injection; dilution of the hydrogen by diluents such as nitrogen, carbon dioxide and carbon monoxide; using EB ventgas to supply a hydrogen and diluent combination; and, using a multiple catalyst bed reactor, or multiple reactors to achieve hydrogenation. In this patent, the written description and drawings of which are hereby incorporated herein by reference in their entirety, a preferred catalyst for the dehydrogenation reaction was palladium on an alumina carrier.

One problem with the above-incorporated PAR process is that the Pd/Al catalyst used in the PAR reactor to dehydrogenate phenylacetylene will continually lose palladium from the alumina carrier until the conversion rate of PA to styrene becomes unacceptably low and the catalyst has to be removed and replaced with new catalyst. Attempts to use various additives to increase conversion of PA to styrene and to increase selectivity of the catalyst from converting styrene to converting PA, have met only minimal success and have not solved the problem of palladium stripping.

SUMMARY OF THE INVENTION

The present invention solves the problems of the prior art by providing an additive when added to conventional PAR systems that not only increases the level of PA conversion, but also stabilizes the catalyst and prevents stripping of the palladium from the alumina base. The additive is one which would normally be utilized as a styrene polymerization inhibitor, in the class of inhibitors consisting of hydroxylamines, as well as combinations of hydroxylamines with phenylene diamines and oxime compounds.

BRIEF DESCRIPTION OF THE DRAWING

The drawing consists of a schematic diagram of a typical styrene purification and polymerization process utilizing a phenylacetylene reduction system having palladium/alumina catalyst and incorporating the inventive process disclosed and claimed herein.

DESCRIPTION OF THE PREFERRED EMBODIMENTS

Figure 1:
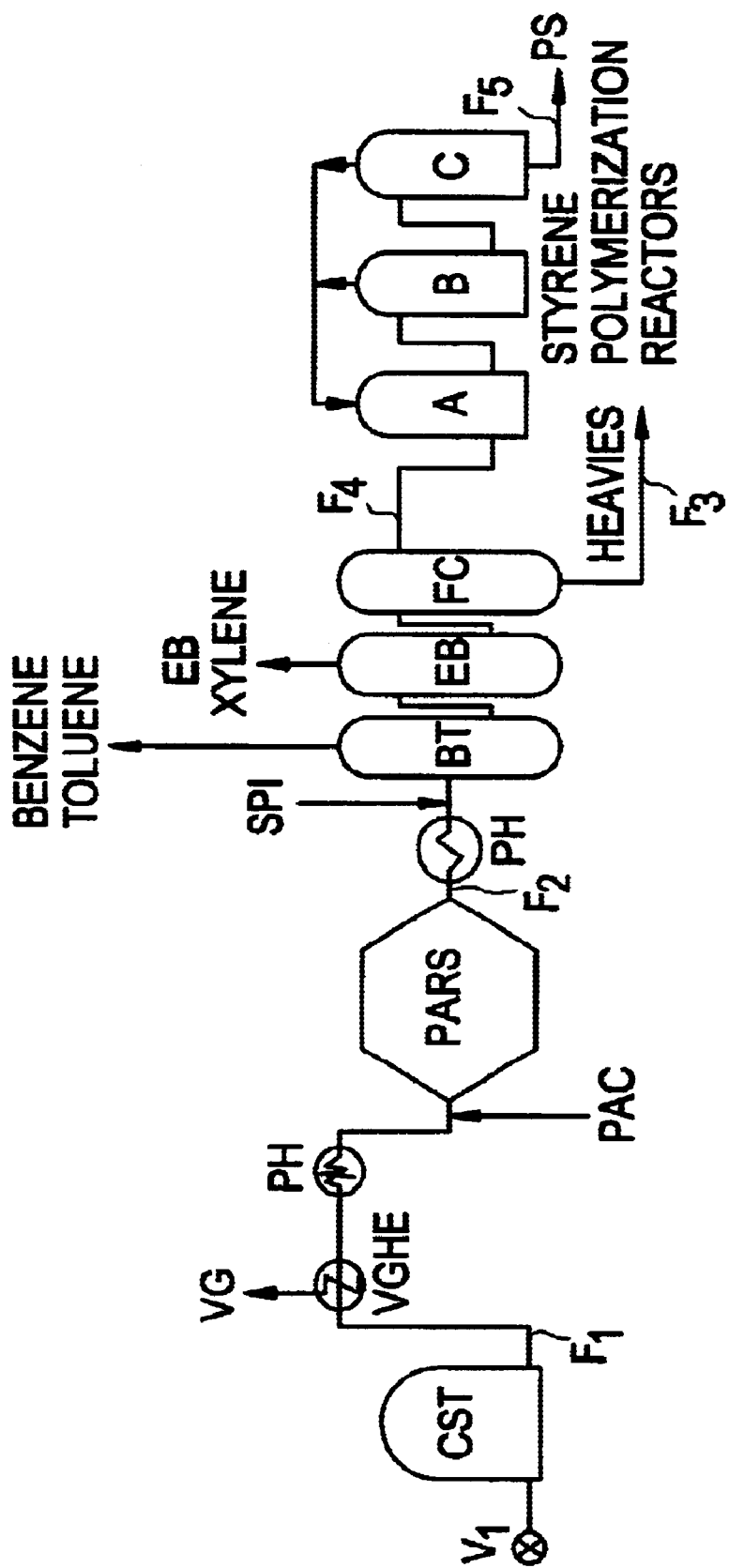

The present invention can more clearly be seen when viewed in conjunction with the illustration of the Drawing. In the illustration, a conventional styrene purification and polymerization process is disclosed. This process is basically similar to that disclosed and fully described in the aforementioned incorporated patent to Butler et al. In the FIGURE, crude styrene which has been manufactured from the dehydrogenation of ethylbenzene, is provided at valve V1, from whence it flows into a crude storage tank CST. From the storage tank, crude styrene flows through flow line F1 through a vent gas heat exchanger VGHE to raise the temperature of the styrene, and from there it is flowed into an optional preheater PH. From the preheater, the crude styrene passes into the phenylacetylene reduction system PARS where the phenylacetylene in the crude styrene is reduced to acceptable level by flowing it over a palladium/alumina catalyst in the presence of hydrogen gas, as more particularly described in the incorporated Butler et al patent.

In a conventional application of this process, a styrene polymerization inhibitor SPI would normally be added to the styrene feed after the preheater PH and immediately prior to the BT Column. This is indicated in the drawing at the input line designated SPI. Since the additive is conventionally known as a styrene polymerization inhibitor, it would not be considered practical or normal to add such a material at any point prior to the BT Column. For example, since this type of inhibitor is water-soluble, to add it to the system as early as valve VI would be a waste of inhibitor material since a large portion of the additive would be dissolved in the water that is normally separated from the styrene monomer in the Crude Styrene Tank CST. The normal amount of styrene polymerization inhibitor added to conventional systems is in the range of about 50 to 500 parts per million.

In the present invention however, it was unexpectedly discovered that by adding a particular styrene polymerization inhibitor to the styrene polymerization system immediately ahead of the phenylacetylene reduction reactor through the phenylacetylene catalyst flowline designated at PAC, an unusual and beneficial result is obtained, which is not predictable by anything heretofore known about the chemistry of such systems. In fact, one would never have expected to obtain results involving phenylactylene reduction by the use of styrene polymerization inhibitors in any portion of a styrene polymerization system. The unexpected result obtained by adding the styrene inhibitor through flowline PAC, at a point not normally associated with polymerization inhibitors, is an increase in phenylacetylene conversion and a stabilization of the palladium on the PAR catalyst.

A particularly advantageous additive for inserting in the feed stream immediately ahead of the PARS is Styrex 310, a commercially available hydroxylamine inhibitor sold by BetzDearbom company located in 4636 Somerton Road Trevose, Pa. 19053. This inhibitor is more particularly described in U.S. Pat. Nos. 5,282,957; 5,396,004; 5,426,257; and, 6,024,894; EP patent 0 594341 A1 and EP patent 0240297 A1. Other patents related to the inhibitor are U.S. Pat. No. 5,221,498; U.S. Pat. No. Pat. No. 5,221,461; U.S. Pat. No. 4,929,778; U.S. Pat. No. 5,221,764; European patent applications 594431 and 87302765; and Canadian patent 2063293.

In one embodiment of the invention, this inhibitor was added to the styrene feed stream directly ahead of the PARS in amounts of around 100 PPM, resulting in an increase in PA conversion of 33% over conventional processes, and a decrease in Palladium stripping from the catalyst to less than 25% of the losses associated with conventional processes using no additives. The following example illustrates the gains associated by using the above-described additive injected in the styrene flowstream in a non-conventional manner.

EXAMPLE

Experiments were conducted in a lab-scale reactor system using the following parameters:

| | |
|---|---|
| Mode | Upflow |
| Pressure | 125 PSI |
| Catalyst | 0.3% by wt. Pd on Al |
| Catalyst Volume | 20 ml, whole extrudates |
| Reactor | 1" OD, 9/16" ID, 1/4" Thermowell |
| Hydrogen rate | 16/1 Molar Hydrogen/PA 13 sccm |
| Fresh feed | 60:40 Styrene:EB, |
| Fresh feed rate | 18 ml/min |
| Feed composition | 200 PPM PA in total reactor feed |
| Additive | Styrex 310, 100 PPM as active material |
| Temperature | 150 degrees F. (65.5 degrees C.) |

The reactor runs using the above described lab scale reactor were conducted with various additives to determine the loss of palladium from the PAR catalyst for each additive. A number of lab runs were conducted to determine the effectiveness of different inhibitors in reducing the level of phenylacetylene in styrene monomer and stabilizing palladium on the catalyst. The following table indicates the results of those runs:

| Additive | Concentration (PPM of active material) | % PD loss after 14 days | PA Conversion wt. % |
|---|---|---|---|
| None | 0 | 19.6 | 60–65 |
| TBC | 7 | 18.0 | |
| TBC | 20 | 21.2 | |
| TBC | 100 | 53.3 | |
| 4-Oxo-TEMPO | 100 | 68.0 | |
| Phenylenediamine | 100 | 54.1 | |
| Nitroxide Radical | 100 | 59.6 | |
| DNBP | 100 | 34.9 | |
| phenyl quinone methide | 100 | 42.7 | |
| Styrex 310 | 100 | 4.8 | 77–84 |

Where TBC is tert-butyl catechol,
DNBP is 2-Sec-butyl-4,6-dinitrophenol

It is clear from the table above, that not only does the preferred additive give much higher conversion of phenylacetylene in styrene, but it also results in far less palladium loss from the catalyst than with other additives. It even cuts palladium loss to less than 25% of the normal loss level when no additives are injected prior to the PAR reactor. This is clearly a highly significant gain due to the higher quality of polystyrene product that can be obtained and also in the tremendous gains in savings from reducing catalyst regeneration and replacement requirements. In the table above, since palladium losses were unacceptably high with all additives but the hydroxylamine (Styrex 310), no conversion figures were listed for them. However, it can be seen from the table that the conversion of phenylacetylene with no additive was in the range of only 60–65 weight percent, whereas the conversion rate for the hydroxylamine runs was in the range of 77–84 weight percent, an average increase in PA conversion of about 30 percent, using the invention, over conventional rates without the invention.

Although a specific preferred embodiment of the present invention has been described in the detailed description and drawing above, the description is not intended to limit the invention to the particular forms or embodiments disclosed therein since they are to be recognized as illustrative rather than restrictive, and it would be obvious to those skilled in the art that the invention is not so limited. For example, whereas a particular phenylenediamine/hydroxylamine additive is disclosed for use in the invention it would be easy to use other analogous additives using similar constituents and homologues. Thus the invention is declared to cover all changes and modifications of the specific examples of the invention, herein disclosed for purposes of illustration, which do not constitute departure from the spirit and scope of the invention.

The embodiments of the invention in which an exclusive property or privilege is claimed are defined as follows:

1. In a styrene purification process wherein a styrene flowstream is processed through a phenylacetylene reactor system to reduce phenylacetylene in said flowstream by hydrogenating it, the improvement comprising the step of adding an additive to the styrene flowstream immediately prior to its entering said phenylacetylene reactor system; wherein said additive comprises a styrene polymerization inhibitor compound.

2. The process of claim 1 wherein said additive comprises an hydroxylamine.

3. The process of claim 1 wherein said additive comprises a phenylamine diamine/hydroxylamine combination.

4. The process of claim 1 wherein said additive is added in amounts of about 1 up to about 300 parts per million.

5. The process of claim 2 wherein said additive is added in amounts of about 1 up to about 300 parts per million.

6. The process of claim 1 wherein said additive comprises an hydroxylamine/oxime combination.

7. The process of claim 2 wherein said additive is added in amounts of about 1 up to about 300 parts per million.

8. A phenylacetylene reduction process for use in a styrene manufacturing system having a phenylacetylene reduction reactor utilizing hydrogen injection to reduce phenylacetylene to styrene, said reduction process comprising injecting effective amounts of a styrene polymerization inhibitor into said manufacturing system immediately upstream of said phenylacetylene reduction reactor.

9. The phenylacetylene reduction process of claim 8 wherein said inhibitor comprises a compound selected from the group consisting of hydroxylamines and combinations of hydroxylamines with oximes and phenylene diamines.

* * * * *